Figure 3:
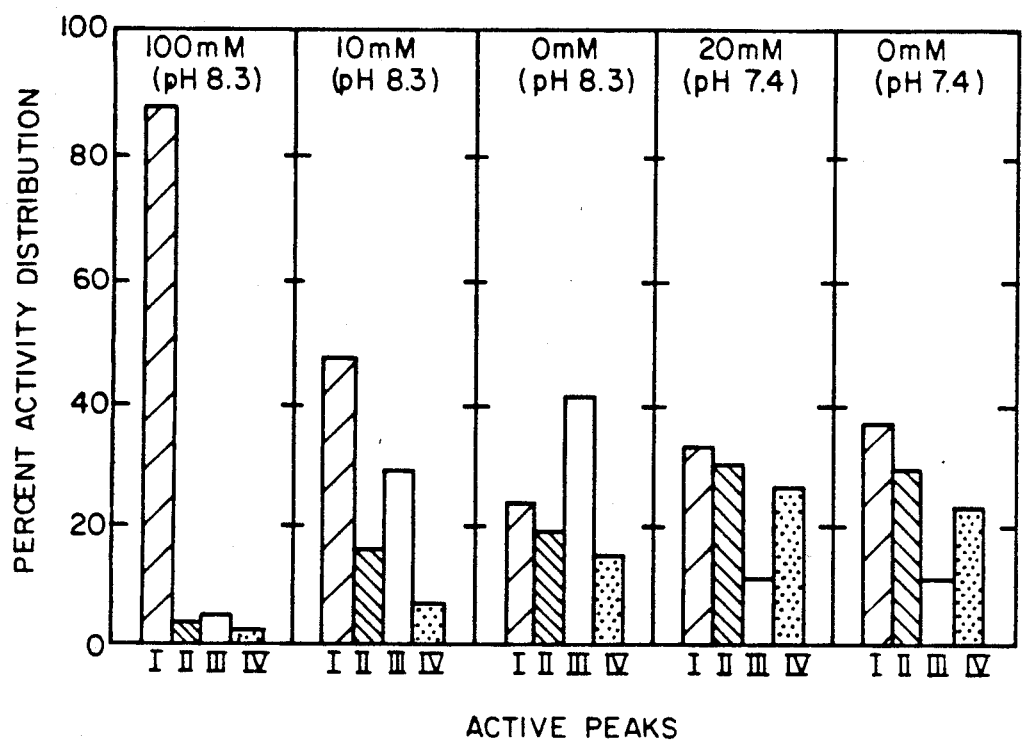

United States Patent [19]

Chen et al.

[11] Patent Number: 5,073,492

[45] Date of Patent: Dec. 17, 1991

[54] SYNERGISTIC COMPOSITION FOR ENDOTHELIAL CELL GROWTH

[75] Inventors: Chung-Ho Chen; Sumi C. Chen, both of Phoenix, Md.

[73] Assignee: The Johns Hopkins University, Baltimore, Md.

[21] Appl. No.: 1,844

[22] Filed: Jan. 9, 1987

[51] Int. Cl.$^5$ .............................................. C12N 5/00
[52] U.S. Cl. ............................ 435/240.2; 435/240.3; 435/240.31; 435/240.23
[58] Field of Search ............... 435/240.1, 240.2, 240.3, 435/240.21, 240.23, 240.31; 530/849; 424/95, 531, 571; 514/2, 21, 42, 43

[56] References Cited

PUBLICATIONS

Chen and Chen, 1985 *Exp. Eye Res.*, 41:77–85, "Purification and Characterization of Two Vascular Endothelium Effectors from Fetal Bovine Retina, Vitreous, and Serum".

D. M. Maurice, "The Location of the Fluid Pump in the Cornea", *J. Physiol.* (1972), 221, pp. 43–54.

*Primary Examiner*—Elizabeth C. Weimar
*Assistant Examiner*—Gail Poulos
*Attorney, Agent, or Firm*—Cushman, Darby & Cushman

[57] ABSTRACT

A method for synergistically enhancing endothelial cell growth in an appropriate environment therefor which comprises adding to the environment, VEGF, effectors and serum-derived factor. A formulation for synergistically enhancing endothelial cell growth comprising VEGF, uridine, thymidine and serum-derived factor is also disclosed.

5 Claims, 3 Drawing Sheets

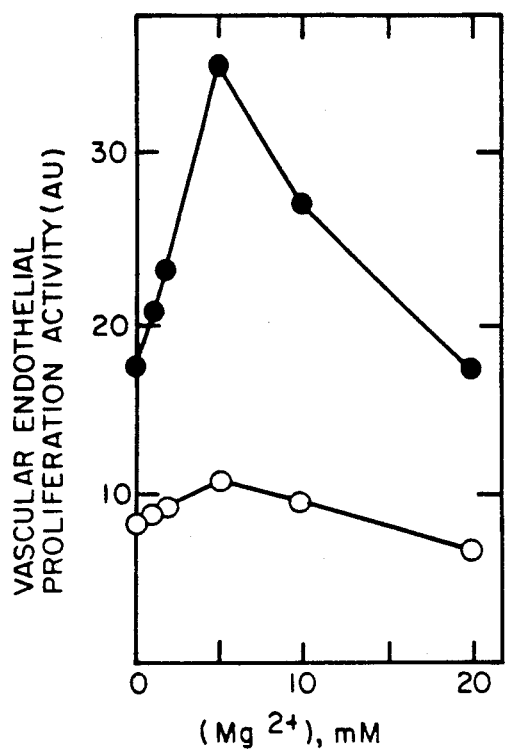
FIG. 1A
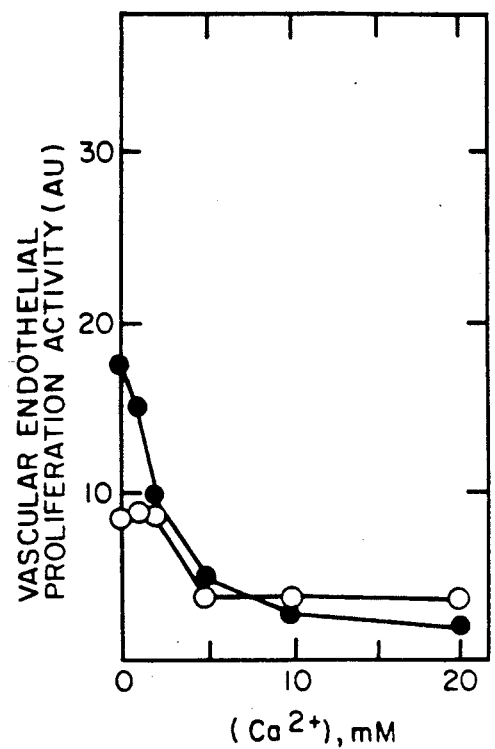
FIG. 1B
FIG. 2
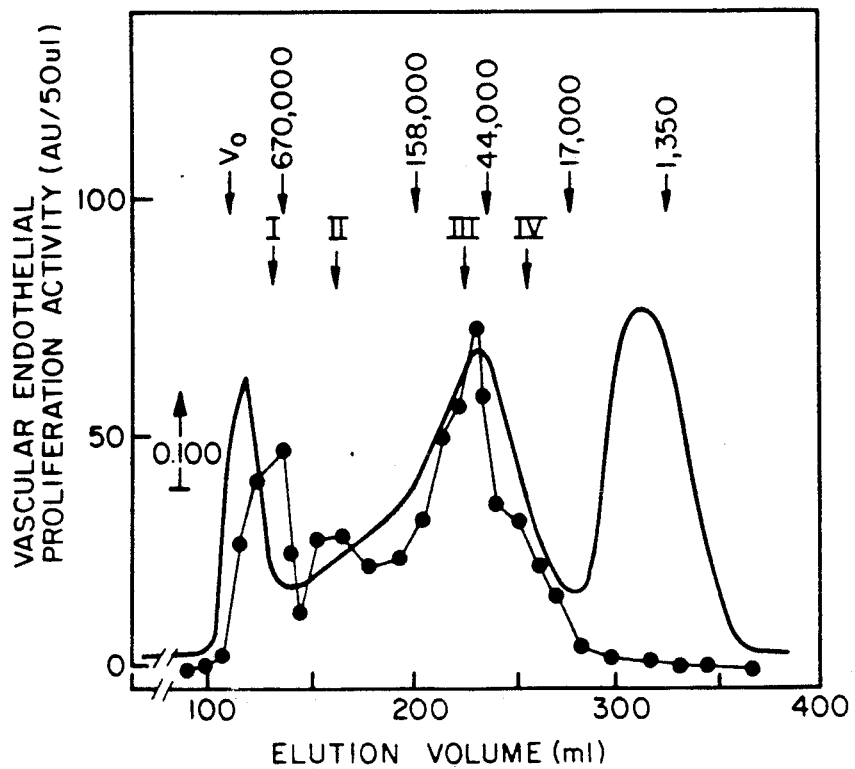

SYNERGISTIC COMPOSITION FOR ENDOTHELIAL CELL GROWTH

The invention is based on work done under grant from the Department of Health and Human Services.

The present invention is concerned with a novel method and composition for synergistically enhancing endothelial cell growth. According to one important aspect of the invention, a formulation is provided which is suitable as an enriching supplement for endothelial cell culture to synergistically improve endothelial cell growth. Other features and uses of the invention will also be evident from the ensuing description thereof.

BACKGROUND TO THE INVENTION

An endothelial cell growth supplement is currently available commercially for use as an additive to enrich endothelial cell cultures and thereby enhance cell growth. The product is a crude preparation from the bovine brain. It is not specific to endothelial cells and stimulates fibroblasts and other cells. A principal object of the invention is to provide a method and formulation for enriching an endothelial cell culture medium to enhance endothelial growth which is specific to endothelial cells.

The invention is based on the finding that the addition of vascular endothelial growth factor (VEGF), vascular endothelial effectors (uridine and thymidine), and a serum-derived factor (SDF), preferably with $Mg^{2+}$, to an endothelial cell culture medium, synergistically and specifically enhances vascular endothelial cell growth.

The mediation of vascular endothelial proliferation by factors in fetal bovine retinal extracts and serum has been described in Exp. Eye Res. 39, 469–478 (1984). This publication discloses that a vascular endothelial growth factor (VEGF) is present in the retina and indicates that this growth factor is synergistic with a factor present in the serum (SDF) in stimulating the proliferation of vascular endothelial cells. The possibility that the retinal factor is the receptor of previously published effectors is also discussed. An earlier paper in IOVS 23, 340–350 (1982) referred to three vascular endothelial cell effectors which had been found in fetal calf retina, vitreous and serum. The molecular nature of these effectors is not disclosed in this 1982 paper.

Another paper in Exp. Eye Res. 41, 77–85 (1985) discloses the purification and characterization of two vascular endothelial effectors from fetal bovine retina, vitreous and serum. The paper describes the purification and characterization of the two effectors as uridine and thymidine, and shows the stoichiometry and the synergism of these effectors with serum-derived factors (SDF) in stimulating the proliferation of vascular endothelial cells. The paper also proposes the biochemical basis of the stimulating effect of the effectors and suggests the possible mechanism of retinal neovascularization mediated by effectors, retinal mitogen (factors) and serum factors. The relationship among effectors, retinal factors and serum factors in stimulating vascular endothelial cell proliferation is not disclosed.

In brief, therefore, the 1984 paper referred to above discloses that a vascular endothelial growth factor (VEGF) is present in the retina and is synergistic with a factor present in the serum in stimulating the proliferation of vascular endothelial cells. The 1985 paper discloses that uridine and thymidine are synergistic with serum factors in stimulating the proliferation of vascular endothelial cells.

The disclosures of the 1984 and 1985 papers are incorporated herein by reference as showing how to obtain the various components used in the present invention.

DESCRIPTION OF THE INVENTION

As noted earlier, the present invention is based on the discovery that an even greater synergistic effect is obtained, in terms of stimulating the proliferation of vascular endothelial cells than hitherto disclosed, by using a combination of VEGF, the effectors uridine and thymidine, and serum-derived factors (SDF). This synergistic effect is much greater than might be expected on the basis of the results obtained using the compositions described in the aforementioned 1984 and 1985 papers (i.e. VEGF and SDF or SDF and effectors, respectively). It has been found that the resulting synergistic combination is specific for stimulating the proliferation of vascular endothelial cells and, to a lesser extent, corneal endothelial cells. As a consequence, the combination can be used as an additive to endothelial cell cultures and human donor cornea storage to enhance the viability and regeneration of endotheliums. Other uses which are contemplated are described later herein.

The synergistic combination of the invention may be prepared in a variety of ways. For example, the components thereof may be mixed together to provide a cell culture enhancement medium or formulation for addition, as desired, to conventional and available endothelial cell cultures. Alternatively, the individual components may be added separately to a cell culture medium to provide the synergistically effective combination of the invention.

The additive may be used with any conventional type of endothelial cell culture or environment. Typically, this includes, for example, the media known as Medium 199 or MEM with Earle's salt or other salts. These media are commercially available. The use of other equivalent media is also contemplated.

The relative proportions of the components used herein can be varied but a synergistically effective composition, normally in sterile aqueous form, will usually comprise, on a weight basis, 20 to 500 parts of VEGF, 0.5 to 5.0 parts of uridine, 0.03 to 0.3 parts of thymidine and 250 to 4000 parts of SDF. The composition will also usually comprise from 20–1020 parts $Mg^{2+}$ to stabilize the VEGF amd maintain its biological activity. The results obtained with $Mg^{+2}$ appear to be specific to the use of this ion. Thus, it has been found that similar results are not obtained using $Ca^{2+}$ which normally would be considered generally equivalent to $Mg^{2+}$.

The VEGF as used to prepare the composition is normally in the form of a sterile aqueous solution or "concentrate" containing 50–150 millimolar NaCl and 10–100 millimolar $MgCl_2$. The pH of this concentrate should be kept in the range of 8.3 to 8.5. Additional $MgCl_2 \cdot 6H_2O$ or the equivalent can be added in formulating the final composition to give the indicated concentration of 20–1020 parts $Mg^{2+}$. There may be situations, for example, when the composition is to be used in vivo, where enough $Mg^{2+}$ is inherently present to accomplish the desired stabilizing of the VEGF. Usually, however, it is necessary to add $Mg^{2+}$ for this purpose, particularly in the case of in vitro uses.

On a concentration basis, the synergistic formulation of the invention will usually comprise, per milliliter, 0.02–0.5 milligrams of VEGF, 0.25–4.0 milligrams of SDF, 2-20 nanomoles uridine, 0.1-1.0 nanomoles thymidine and 0.5-5.0 micromoles $Mg^{2+}$. The proportions given for VEGF and SDF are based on the use of these materials in crude form, i.e. VEGF as extracted from retina cells and SDF as dialyzed serum. If these materials are purified, the quantities thereof which are used should be calculated on the basis of the biological activities for the crude materials.

The synergistic additive of the invention will generally be used with cell cultures at temperatures in the range of 34° C. to 37° C. and at a pH of 7.4 to 7.6 although it will be recognized that temperatures and pHs outside these ranges may also be suitable in certain circumstances.

The VEGF used herein can be obtained from fetal bovine retina as described in the 1984 and 1985 publications referred to earlier herein. However, the VEGF may also be obtained from other sources.

The SDF may be derived from fetal bovine serum as described in said earlier publications. However, growth factor derived from other types of serum including, for example, human serum, can also be used for present purposes. Uridine, thymidine and magnesium chloride hexahydrate ($MgCl_2 \cdot 6H_2O$) are commercially available and these may be obtained for use herein from any convenient source.

The invention and its unique advantages are illustrated by the following examples and discussion. For possible ease of reference, the following abbreviations are used to refer to the indicated materials:

| Abbreviation | Material |
| --- | --- |
| VEGF | vascular endothelial growth factor |
| SDF | serum-derived growth factor |
| FBR | fetal bovine retina |
| FBS | fetal bovine serum |
| FGF | fibroblast growth factor |
| EGF | epidermal growth factor |
| FAE | fetal aortic endothelial cells |
| MEM | minimum essential medium |

EXAMPLES

Cell proliferation assays were conducted by adding (a) SDF; (b) SDF and effectors; (c) SDF and VEGF; (d) SDF, VEGF and the effectors; and (e) fetal bovine serum (FBS) to an endothelial cell growth medium. Cell proliferation activity was determined for each additive. Agarose chromatography was also carried out. The assays were conducted both in the presence and absence of $Mg^{2+}$ and at various pHs to determine the significance of these features. Further tests were conducted using $Ca^{2+}$ in lieu of $Mg^{2+}$. Cell specificity of VEGF was also compared to EFG, FGF and insulin.

Fetal bovine serum (FBS), FGF, EGF, insulin and tissue culture medium as used were obtained from commercial sources. Fetal bovine retina (FBR) as used herein was isolated from the fetal bovine eyes obtained from a local slaughterhouse within one to two hours after they were enucleated. Unless otherwise indicated, FBR were extracted with 10 mM Tris HCl buffer, pH 7.4, exactly as described in the 1984 paper referred to earlier. Dialyzed serum was prepared by dialyzing FBS against excess volume of ice-cold 50 mM NaCl for 6 hours using Spectropor tubing (12,000-14,000 molecular weight cut-off).

Cell Proliferation Activity Assays

Quantitation of cell proliferation activity was carried out in known fashion. See Chen et al, *Exp. Cell Res.* 136, 43 (1981). The cells were plated at 30 to $35 \times 10^3$ cells per well. After cultivation for 4 hrs., the cells from a set of six wells were harvested and counted (three times per well) with a Coulter cell counter to obtain an average of initial cell counts ($N_o$). For other wells, the medium was changed to assay fluid (1 ml per well) and samples were added. After further cultivation for 41 to 46 hrs., the cells were harvested and counted to obtain a total cell count, $N_t$. Assays were performed in triplicate. The experimental error, including cell harvestings and countings, was less than 10%. For fibroblasts (BALB/c 3T3 and Swiss 3T3), Dulbecco's modified minimum essential medium (DMEM) supplemented with 10% FBS was used for subcultures and DMEM with 3 mg/ml dialyzed FBS (dFBS) was used as the assay fluid. For other cell lines, MEM with Earle's salts (EMEM) and 10% FBS was used for subcultures; Medium 199 with 3 mg/ml dFBS was used as the assay fluid. When effectors were supplemented in the assay fluid, uridine and thymidine were added at 10 and 0.5 uM, respectively. Where crude dFBS and dialyzed FBR (dFBR) were used as the sources of serum-derived factor (SDF) and vascular endothelium growth factor (VEGF), respectively, the data represent only the activity of the actual materials used. Activity of both crude preparations varies from preparation to preparation. A marked variation in results may occur when activity of the crude preparations is at extreme range. For cell-specificity study, peak I of FBR agarose chromatography (cf. FIG. 2) was used because of a higher specific activity. Experiments with other peaks showed similar results.

Cell proliferation activity was calculated on the basis of the normalized cell growth rate using the formula: $1/(T - T_{min})$, where T is the average length of cell duplication cycle, in hrs per cell cycle, and $T_{min}$ is minimum T under optimal culture conditions. T is the reciprocal of average cell duplication frequency, f (in cell cycles per day), which is calculated in known fashion according to the equation: $f = 1/(0.301 \, t) \, (\log N_t - \log N_o)$. One arbitrary unit (AU) of cell proliferation activity is defined as a mitogen-elicited normalized cell growth rate of 0.2 cell cycles per day. The kinetic constant $T_{min}$ was routinely determined using FBS as the source of stimuli, with concentrations varying from 0 to 4.5 mg/ml.

Fetal bovine aortic endothelial cells (FAE) were isolated and maintained as described by Chen et al, *Invest. Ophthal. Vis. Sci.* 23 (1982) 340. The cells were used at the 9th to 18th passages. Corneal epithelial and endothelial cells were isolated by gently scraping off the cells from the tissue surfaces with the tip of a one-ml disposal pipette. The isolated cells were implanted in EMEM supplemented with 20% FBS. For the isolation of keratocytes, both endothelial and epithelial layers were peeled off from the corneal button; the remaining stromal layer was implanted in EMEM containing 20% FBS. For lens epithelial cells, the capsule along with the epithelium was removed and implanted. The cells were subcultured (the first serial passage) after 14 days, and were re-fed with fresh EMEM containing 10% FBS every two to three days. The cells were used at the 4th to 7th passages. Walker 256 carcinoma, and BALB/c and Swiss 3T3 fibroblasts were obtained from American Type Culture Collections, Inc. (Rockville, Md.).

Agarose Chromatography

A column (2.5×58 cm, $V_t$=330 ml) packed with Bio-Gel A-1.5m, 100-200 mess was equilibrated with buffer as indicated in the figures and tables presenting the results. The chromatograph was developed with the column buffer at a flow rate of 24 ml/hr at 4° C. Three-ml fractions were collected. Absorbence of effluent was simultaneously monitored with a UV monitor at 80 nm (LKB UVicord S). Selected fractions were assayed for the cell proliferation activity using FAE.

Referring now to the drawings, FIGS. 1A and B show the effect of $Mg^{2+}$ and $Ca^{2+}$ on the vascular endothelial proliferation activity. The assay fluid consisted of Medium 199 and 3 mg/ml dFBS, with (●—●) or without (○—○) 0.1 mg/ml dialyzed FBR.

FIG. 2 shows the results of agarose chromatography of fetal bovine retinal extract (FBR). FBR (310 mg) in 150 mM NaCl, 10 mM $MgCl_2$, and 20 mM Tris HCl, pH 8.3, was chromatographed with a Bio-Gel A-1.5m column (2.5×58 cm) equilibrated with the same buffer. The solid line in FIG. 2 indicates the absorbence at 280 nm. The column was calibrated with proteins of known molecular weights as indicated: blue dextran ($V_0$, 2,000,000); thyroglobulin, 670,000; IgG, 158,000; ovalbumin, 44,000; myoglobin, 17,000; and Vitamin $B_{12}$, 1,350. Active peaks are indicated in Roman numerals.

FIG. 3 shows the effect of $Mg^{2+}$ and pH on the VEGF activity distribution in the peaks separated by agarose chromatography. FBR samples in 150 mM NaCl and 20 mM Tris HCl were pre-treated with various concentrations of $Mg^{2+}$ at pH 7.4 or 8.3, as indicated in the figure. The column was equilibrated with the sample buffer for the chromatography of samples containing no $Mg^{2+}$, or with the buffer containing 10 mM $Mg^{2+}$ for the chromatography of samples pre-treated with $Mg^{2+}$. Activity distribution is expressed in terms of percent of total activity recovered.

Figure 4A:
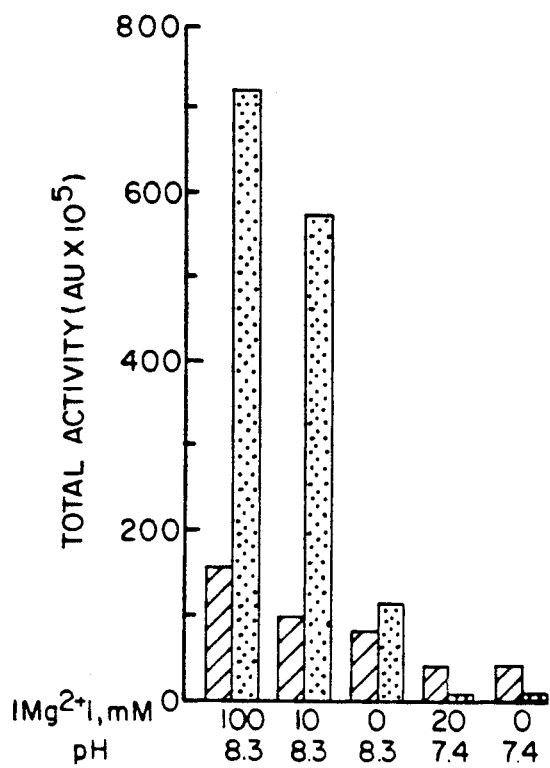
Figure 4B:
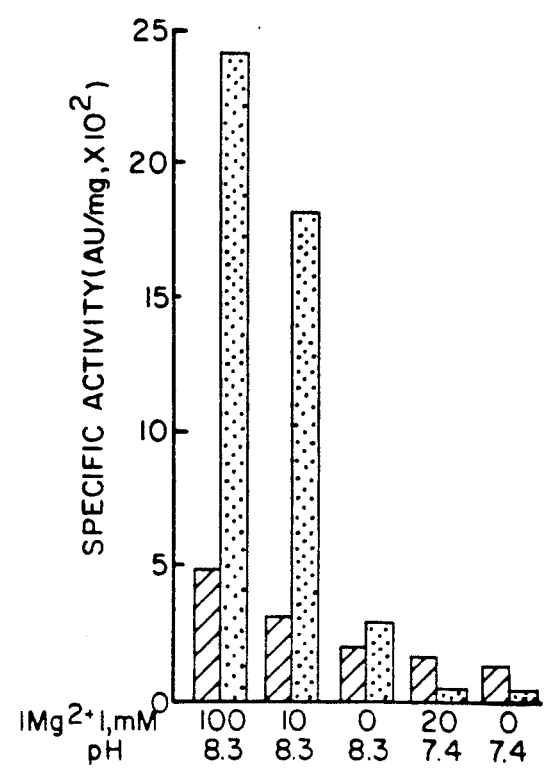

FIGS. 4A and 4B shows the effect of $Mg^{2+}$ and pH on the total and specific activity of VEGF before and after agarose chromatography. Data were calculated from the same set of experiments as shown in FIG. 3 in terms of total activity (A) and specific activity (B). The dotted bar is before chromatrography while the clear bar is after chromatrography.

Figure 5:
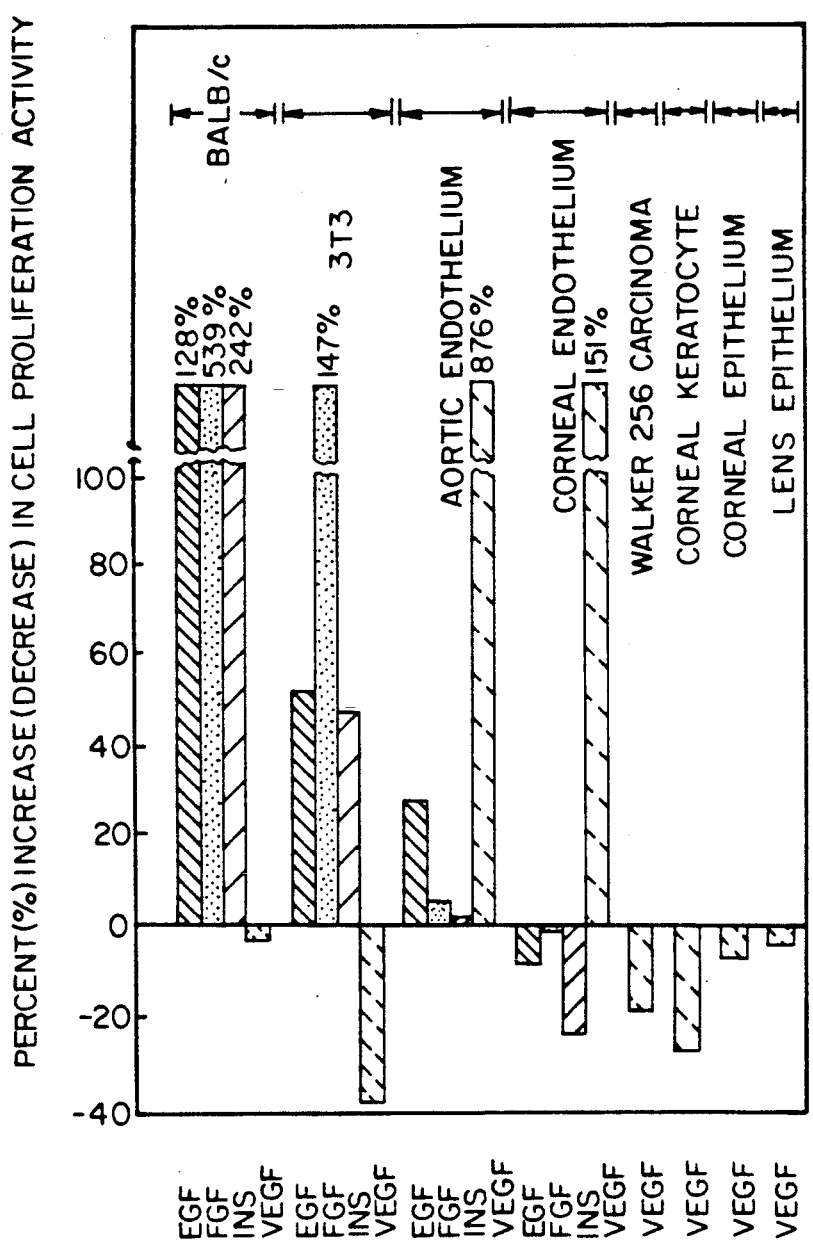

FIG. 5 shows the cell-specificity of VEGF compared with EGF, FGF, and insulin. The assay fluid was supplemented with 3 mg/ml dFBS, 10 uM uridine, and 0.5 uM thymidine. When added, EGF was 0.025 ug/ml; FGF, 0.1 ug/ml; insulin, 0.5 ug/ml; and partially-purified VEGF (peak I of FIG. 2), 5 ug/ml.

The remarkable synergistic effect obtained using the combination of VEGF, vascular endothelium effectors (uridine and thymidine) and SDF, according to the invention, to stimulate vascular endothelial cell proliferation is shown in Table 1 where the results so obtained are compared with the results obtained using SDF alone, SDF and the effectors only, SDF and VEGF only or FBS alone.

TABLE 1

| Additions* | Cell Proliferation Activity (AU) |
| --- | --- |
| SDF | 13.5 |
| SDF, effectors | 83.0 |
| SDF, VEGF | 62.3 |
| SDF, effectors, VEGF | 285.0 |
| 10% FBS | 98.5 |

*Medium 199 was employed as the assay fluid. Dialyzed fetal bovine serum (dFBS) (3 mg/ml) was used as the source of SDF (serum-derived factor). Vascular endothelium effectors were 10 uM uridine and 0.5 uM thymidine. Dialyzed FBR (0.1 mg/ml) was the source of VEGF.

As will be evident, the combination of SDF, effectors and VEGF demonstrated much greater cell proliferation activity than the other additives.

The advantages of the invention are further shown in Table 2. The data presented in Table 2 illustrates the effect of effectors (uridine and thymidine) and VEGF on $T_{min}$ on vascular endothelial cell growth in the presence of dialyzed FBS. For this purpose, $T_{min}$ was determined using fetal bovine serum (FBS) or dFBS with concentrations varying from 0 to 4.5 mg/ml. Uridine (Urd) and thymidine (dThd) were added at a final concentration of 10 uM and 0.5 uM, respectively. Partially-purified VEGF was added at about 2 ug/ml (specific activity=$4.7\times10^4$ AU/mg). Fetal bovine aortic endothelial cells at the 17th to 21st passages were used. The data presented represents the average of four measurements in "means±standard deviation". Probability of difference from that obtained with FBS as stimulus is shown in parentheses.

TABLE 2

| Mitogen Components | $T_{min}$ (hrs/cell cycle) |
| --- | --- |
| FBS | 17.7 ± 0.5 |
| dFBS + Urd + dThd | 18.3 ± 0.4 (p = 0.14) |
| dFBS + VEGF | 17.2 ± 0.7 (p = 0.31) |
| dFBS + Urd + dThd + VEGF | 15.4 ± 0.6 (p = 0.004) |

As will be evident, the combination of serum, effectors (uridine and thymidine) and VEGF substantially lowered the $T_{min}$.

The results of the experiments referred to in the foregoing and in the drawings are further discussed hereinafter:

Stimulatory Characteristics

Previously, it had been shown that the serum-derived factor (SDF) in dFBS exhibited a marked synergistic effect with VEGF in the retina (Exp. Eye Res. 39, 1984, 469) and with purified vascular endothelium effectors (Invest. Ophthal. Vis. Sci. 23, 1982, 340 and Exp. Eye Res. 41, 1985, 77) in bringing about the stimulation of vascular endothelial cell proliferation. As shown in Table 1, the stimulatory effects of these three types of substances are synergistic, not additive. In the presence of 10 uM uridine, 0.5 uM thymidine, 3 mg/ml dFBS, and 0.1 mg/ml dFBR, the actively growing FAE were stimulated to proliferate at a rate about three times that obtained with 10% FBS. In the presence of all three types of mitogenic substances, $T_{min}$ was significantly shortened (P<0.01) (Table 2). No significantly shortened $T_{min}$ was observed when either VEGF or effectors were absent.

Effect of Divalent Cations in the Assay Fluid

As shown in FIG. 1a, stimulation of FAE proliferation brought about by dFBS and retinal extract was further enhanced by the addition of $Mg^{2+}$. A two-fold increase in cell proliferation activity was observed with the addition of 5 mM $Mg^{2+}$ providing a total $Mg^{2+}$ concentration in the medium of 5.8 mM. Addition of $Mg^{2+}$ to a higher concentration exerted a retardation effect. $Mg^{2+}$ elicited no significant effect on cell proliferation activity in the absence of retinal extract (FIG. 1a). This observation indicates that the effect may be brought about by an interaction between $Mg^{2+}$ and VEGF at the molecular level. It is also to be noted that $Mg^{2+}$ appears to be the specific cation for such an interaction. Calcium ion, the element below magnesium in Group IIa of the element periodic table, exerted a concentration-dependent retardation effect in the presence or absence of retinal extract (FIG. 1b). Other divalent cations with greater atomic weights also exerted a cell-retardation effect at concentrations greater than 0.1 mM. However, because about 1.8 mM $Ca^{2+}$ is present in the pre-formulated culture medium, it is possible that $Ca^{2+}$ may have a stimulatory effect at lower concentration.

Chromatographic pattern of VEGF activity

In the permeation chromatography using agarose with a molecular weight permeation range up to $1.5 \times 10^6$, mitogenic activity in FBR was fractionated into four distinct peaks in addition to the peak near the end of the column volume (FIG. 2). The latter peak was absent in FBR dialyzed against $H_2O$ or 10 mM Tris HCl buffer, pH 7.4, and was the source of dialyzable vascular endothelium effectors. Molecular weight of the smallest component in these active peaks was estimated to be about 25,000 (FIG. 2). The distribution patterns of these four distinct peaks are dependent on pH and $Mg^{2+}$ concentration. At an alkaline pH (8.3) and with a high $Mg^{2+}$ concentration, more VEGF activity was distributed in the high molecular weigh component peak (FIG. 3).

As shown in FIG. 4, both the total and the specific activities of VEGF in FBR is significantly enhanced by treating samples with $Mg^{2+}$ at pH 8.3. The activity, both total and specific, is further elevated following agarose chromatography. The extent of increase is $Mg^{2+}$-concentration dependent. With $Mg^{2+}$ in the FBR samples at a concentration of 100 mM, 4- and 5-fold increases in the total and the specific activities, respectively, were observed following agarose chromatography. At pH 7.4, a similar effect of $Mg^{2+}$ on VEGF activity was not observed; both the total and the specific activities recovered from the agarose chromatographic fractionations were reduced by 80%, with or without $Mg^{2+}$ treatment.

Cell Specificity

FIG. 5 shows that VEGF in the FBR samples is extremely potent for stimulating the growth of FAE, and at a lesser extent, rabbit corneal endothelial cell. VEGF has no stimulatory effect on all other cell lines examined, but rather exhibits various degrees of retardation effect on other cell lines examined. These include two fibroblasts lines (BALB/c and Swiss 3T3), one tumor cell line (Walker 256 carcinoma), the lens epithelial cells, and two other corneal cells (epithelial cells and stromal keratocytes). In terms of the stimulatory effect on fibroblasts and endothelial cells, VEGF in the FBR samples is distinctly different from insulin, FGF, and EGF (FIG. 5). VEGF exhibits a remarkable stimulatory effect on endothelial cell proliferation, but it exerts a significant retardation on the growth of mouse 3T3 fibroblasts and a slight retardation on the growth of BALB/c 3T3 fibroblasts. By contrast, under present assay conditions, insulin, FGF, and EGF elicit a remarkably enhanced proliferation of BALB/c 3T3 fibroblasts, and at a lesser extent, the proliferation of mouse 3T3 fibroblasts. These mitogens, however, exhibit only a negligible stimulatory effect on FAE, and a retardation effect on the growth of corneal endothelial cells.

The foregoing reveals several important points:

1. When combined, VEGF, SDF and the vascular endothelium effectors (uridine and thymidine) exhibit a pronounced synergism in bringing about an enhanced vascular endothelial cell proliferation with a shortened $T_{min}$;

2. VEGF, which is a polypeptide in the retina, shows a multiplicity upon agarose chromatography with the 25,000-dalton component as the smallest subunit;

3. In in vitro experiments, $Mg^{2+}$ is the specific divalent cation that, at 100 mM, retains the VEGF molecule in the crude FBR in the aggregated form and brings about a total activity recovery five times greater than the calculated value;

4. VEGF is highly specific for endothelial cells and is distinctly different from FGF, EGF, and insulin in terms of molecular weights and cell-specificity.

Blood is known to contain insulin, and FGF activity and the stimulation of fibroblast proliferation by EGF has been previously reported. Based on these findings and observations 1 and 4 above, it is clear that VEGF is of retinal origin, not from blood contamination in the retinal tissue preparation. Several lines of evidence suggest that VEGF and other growth factor isolated from bovine retina (ECGF) probably are different molecules. VEGF is a slightly larger molecule; VEGF activity is nearly abolished under the chromatographic condition using high NaCl concentration gradient that isolates ECGF. Furthermore, unlike ECGF, VEGF elicits no stimulatory effect on fibroblasts, and the stimulatory effect of VEGF is SDF-dependent and is enhanced by $Mg^{2+}$, uridine and thymidine. Thus, the foregoing results indicate that VEGF possesses characteristic properties that are unique or at least have not been previously reported for other growth factors. Therefore, VEGF is believed to represent a new type of growth factor that is highly specific for vascular endothelial cells. The detection of VEGF requires the presence of SDF and effectors at optimal concentrations.

As noted earlier, synergism between SDF and effectors (uridine and thymidine) and between SDF and VEGF has been previously reported. The present invention, however, shows that, when combined, SDF, VEGF and the effectors exhibit a much greater synergism. In the absence of SDF, effectors and VEGF exert no significant stimulatory effect (see again Exp. Eye Res. 39 (1984) 469 and 41 (1985) 77). Thus, the present invention indicates that stimulation of vascular endothelial cell proliferation is coordinated by three closely interrelated components: SDF, vascular endothelium effectors, and VEGF. SDF is collectively denoted, but not highly defined to represent a group of serum factors that, in conjunction with VEGF and effectors, mediate the cellular activities such as pyrimidine uptake and uridine and thymidine kinase activation. Previous experiments have shown that SDF-induced activation of uridine and thymidine kinases in FAE accounted for the stimulatory effect of two purified effectors. The biochemical basis of the stimulatory effect of VEGF is not fully understood but, based on the molecular nature of the two purified effectors and the shortened cell cycle (Table 2), it is possible that these inter-related mitogenic substances coordinatelly potentiate the cellular activities in the $G_1$ phase; namely, protein biosynthesis and metabolism. The reduction in the duration of the $G_1$ phase has previously been suggested to account for shortening the cell cycle.

Effects of $Mg^{2+}$ exerted on VEGF is of interest. In in vitro experiments, $Mg^{2+}$ at high concentrations (>10 mM) helps retain the VEGF molecule in the biologically active folding-orientation or aggregation form. Since the cellular $Mg^{2+}$ concentration is less than 2 mM, most VEGF molecules in vivo probably are in the dissociated form. Because assay fluid contains $Mg^{2+}$ and because the addition of chelating agents will cause cell detachment, the effect of divalent cation antagonists on the activity of VEGF cannot be studied in in vitro experiments using cell culture. However, it appears that VEGF activity is irreversibly abolished when the sample is treated with a high concentration of NaCl in the absence of $Mg^{2+}$, and the inactivation is prevented when $Mg^{2+}$ is present. This observation raises the possibility that $Mg^{2+}$ may help maintain the VEGF molecule in certain configurations for a greater stability. $Mg^{2+}$ was found to be the specific divalent cation for such an inter-molecule interaction. Presumably, $Mg^{2+}$ has an atomic dimension for best space-fittig for the VEGF molecule. The $Mg^{2+}$ effects similar to that observed with VEGF have not been reported with other known growth factors. However, $Mg^{2+}$ exerted no effect on FGF and EGF examined with both fibroblasts and FAE (unpublished observations).

Furthermore, at least to some extent, the enhanced cell proliferation activity may be brought about by $Mg^{2+}$-related cellular activity. For instance, $Mg^{2+}$ is known to be needed for numerous enzymatic reactions, including uridine kinase. $Mg^{2+}$ has also been reported to enhance the uptake of uridine and nutrients by fibroblasts.

The utility of the various aspects of the invention will be evident to those in the art. VEGF together with uridine and thymidine, has a potential application for the prevention or treatment of diseases with etiology related to vascular endothelial cell degeneration. Additionally, VEGF, together with uridine, thymidine, and $Mg^{2+}$, is useful for topical application on wound healing. When combined, VEGF, SDF, uridine, thymidine, and $Mg^{2+}$ can be applied to cell culture as an enrichment medium, to organ transplant or the like to promote grafting, and to human donor cornea storage to enhance the viability and regeneration of endothelium. Derivatives and/or antibodies of VEGF may also be useful for the treatment of proliferative vascular diseases such as proliferative retinopathies and inflammation and VEGF antibodies can be used in a diagnostic kit for detecting vascular disorders.

In vivo, capillary endothelial cells hardly divide. However, these cells proliferate under pathological conditions or when the blood vessels are injured. In vivo experiments show that, when retinal capillaries are induced to proliferate into the vitreous body, effectors in the vitreous are exhausted and SDF concentration is parallel with the capillary proliferation activity. The results obtained from cell culture and in vivo experiments indicate that capillary endothelial cell proliferation is closely regulated by VEGF, SDF, uridine, and thymidine (together with $Mg^{2+}$) in terms of integrity and concentration of these components. Uridine, thymidine and $Mg^{2+}$ are also present in the cells, and they are released into the extracellular space when the cells are damaged. SDF exists in the blood circulation and VEGF is present in the retina (a highly vascularized tissue). Possible localization of VEGF in other tissues has not been exhaustically studied. VEGF is released when the cells are damages.

Vascular disorder-related diseases are the major causes of death and blindness in the world. Examples of these diseases are stroke, heart attack, angine pectoris, atherosclerosis, retrolental fibroplasia, and proliferative retinopathies. Although the etiology and pathogenesis of all these diseases may vary, they are associated to some extent with either the constriction or obliteration of blood vessels, the degeneration or necrosis of cells in blood vessels, the degeneration or necrosis of cells in blood vessel linings, or the malfunction or abnormal metabolic activity of blood vessels.

Work in prostaglandins reveals the involvement of enzymes of both platelets and vascular endothelial cells in the regulation of platelet clumping and arterial constriction. In other words, the enzymatic activities involved in prostaglandin pathways have to be properly balanced and regulated in order to maintain a normal blood flow for nourishment of tissues, removal of metabolic wastes, and proper blood coagulation when necessary. However, in most cases, vascular disorder-related diseases possibly may be due to not only the malfunction of prostaglandin pathways but also to failures in enzymatic activity or the degeneration of vascular endothelial cells. Thus, insufficient blood flow or ischemia, especially in peripheral areas, may occur due to the degeneration of cells in blood vessel linings, or to the constriction of blood vessels and platelet clumping. These have been documented in retinopathies, which can be readily observed by indirect ophthalmoscopy or fluorescein angiography. In the retina, neovascularization frequently occurs adjacent to the constricted or obliterated retinal vessels following ischemia, in which endothelial cells are degenerated. However, these new vessels are not healthy. Hemorrhage and leakage of dye are their characteristic features.

Importantly, these vascular disorder-related diseases are chronic in nature; they take years to develop. The vascular disorders may proceed without being noticeable until the victims are stricken by the vascular disorder-related diseases. In humans, these diseases are usually manifested during middle age or later, except for juvenile-onset diabetics who may develop such diseases in their 20's or younger. (In premature infants, retrolental fibroplasia takes palce immediately following oxygen therapy.) These vascular disorders are not found in normal and metabolically active children and yound persons. Therefore, viability and mitoticability (or regenerability) of vascular endothelial cells are probably the key in determining the manifestation of vascular disorders, and they could be dramatically reduced in the event of aging and/or metabolic failure such as in diabetes.

In addition to the vascular disorders related to endothelial degeneration, there is another type of vascular disorders, that associated with the proliferation of capillary endothelium. Examples of the disorders include proliferative retinopathies where abnormal blood vessels proliferate from the retina into the vitreous body, and the tumor invasion where massive new capillaries proliferate from the adjacent host tissue towards the invaded tumor.

In the retinopathy, abnormal new vessel formation (neovascularization) occurs at the sites adjacent to the necrotic retina. It is thought that neovascularization is initiated by chemical signals released from the necrotic tissues and from the invaded tumors.

Wound healing and immune reactions are another unique case, in which capillary endothelial cell regeneration and capillary proliferation take place. Chemical signals which may account for the initiation of these vascular reactions have not been documented.

Clearly, endothelial proliferation, regeneration or degeneration is a major event in the vascular disorders or reactions regardless of etiology of the diseases. The therapeutic applications of VEGF referred to above are consistent with the biological activity of endothelium in these diseases and the biological functions of VEGF and its synergistic components, particularly as contemplated herein.

In addition to these therapeutic applications, VEGF in the combination contemplated herein has a potential application in the extended storage of human donor corneas. During the period of storage, endothelium of isolated donor corneas deteriorates. In vivo, the single-cell-layer endothelium functions as the biochemical and physiological barrier of the cornea. Isolated donor corneas with degenerated endothelium cannot be used for the transplant. The addition of the synergistic combination of the invention in the storage medium prevents the degeneration of endothelium, maintains the active metabolic state of the endothelium, and enhances the regeneration ability of the tissue.

VEGF and its antibodies are useful in the studies on the biochemistry and biological functions of vascular endothelial cells using cell cultures. Because VEGF is a specific mitogen for the vascular endothelial cells, VEGF is particularly useful for the isolation and culture of pure endothelial cells for these studies.

SUMMARY

To summarize, it is shown above that a vascular endothelial cell growth factor (VEGF) in the retina exhibits pronounced synergism with the serum-derived factor (SDF) and the vascular endothelium effectors in stimulating the proliferation of vascular endothelial cells. VEGF shows a chromatographic multiplicity with the 25,000-dalton component as the smallest subunit. $Mg^{2+}$ is a specific divalent cation that retains the VEGF molecule in the aggregated form and enhances the activity, both total and specific. VEGF is highly specific for endothelial cells and is distinctly different from FGF, EGF, and insulin in terms of molecular weight and cell-specificity. Under the indicated assay conditions, VEGF has no stimulatory effect on other cell lines examined, including lens epithelial cells, corneal epithelial cells, corneal keratocytes, Walker 256 carcinoma, and fibroblasts.

It will be recognized that various modifications may be made in the invention and its uses as described in the foregoing. It is contemplated, for example, that the compositions may be used both in vitro and in vivo to stimulate the proliferation of vascular endothelial cells. Clinically, the compositions may be used topically to promote endothelial cell growth in the case of, for example, burns. The compositions may also be useful to promote grafting for organ transplants or the like. The effective growth of endothelial cells in vitro for biological study is also visualized along with other research and clinical uses, e.g. for cornea storage or the like. Other uses are also evident from the foregoing. Accordingly, the scope of the invention is defined in the attached claims wherein:

We claim:

1. A method for synergistically enhancing endothelial cell growth in an in vitro culture which comprises adding to said culture, VEGF, uridine, thymidine and serum-derived factor in synergistically effective amount.

2. The method of claim 1 wherein a source of $Mg^{2+}$ is also included to stabilize the VEGF.

3. A formulation for synergistically enhancing endothelial cell growth in vitro consisting essentially of a synergistically effective mixture of VEGF, uridine, thymidine and serum-derived factor.

4. The formulation of claim 3 including a source of $Mg^{2+}$.

5. The formulation of claim 3 in sterile aqueous form.

* * * * *